| United States Patent [19] | [11] Patent Number: 4,529,818 |
| Nesheiwat et al. | [45] Date of Patent: Jul. 16, 1985 |

[54] CONTINUOUS PROCESS FOR THE PRODUCTION OF ALKALI METAL N-METHYLAMINOBUTYRATE

[75] Inventors: Afif M. Nesheiwat; Fred T. Sherk, both of Bartlesville, Okla.

[73] Assignee: Phillips Petroleum Company, Bartlesville, Okla.

[21] Appl. No.: 502,032

[22] Filed: Jun. 7, 1983

[51] Int. Cl.³ ............................................. C07C 101/04
[52] U.S. Cl. ...................................... 562/553; 562/556
[58] Field of Search ................................ 562/553, 556

[56] References Cited

U.S. PATENT DOCUMENTS

| 3,867,356 | 2/1975 | Campbell | 260/79.1 |
| 3,919,177 | 11/1975 | Campbell | 260/79.1 |
| 4,060,520 | 11/1977 | Irvin | 260/79.1 |
| 4,371,706 | 2/1983 | Edmonds | 562/553 |

*Primary Examiner*—Michael L. Shippen

[57] ABSTRACT

A process for producing alkali metal aminobutyrate or alkali metal aminobutyrate-alkali metal bisulfide complex by contacting an aqueous alkali metal hydroxide with NMP and optionally alkali metal bisulfide in a stirred reactor under reaction conditions to produce a predominantly one-phase system and maintaining these reaction conditions while passing the one-phase system through a disrupted flow tube reactor to complete the reaction. Dehydrating the reaction product in a two-stage dehydration process using a higher temperature in the second stage.

14 Claims, 2 Drawing Figures

CONTINUOUS PROCESS FOR THE PRODUCTION OF ALKALI METAL N-METHYLAMINOBUTYRATE

BACKGROUND OF THE INVENTION

This invention relates to alkali metal N-methylaminobutyrates. In one of its aspects this invention relates to a continuous process for making alkali metal N-methylaminobutyrate. In still another aspect of this invention it relates to the preparation of dehydrated slurries of alkali metal N-methylaminobutyrate. In still another aspect of the invention it relates to the preparation of complexes of alkali metal N-methylaminobutyrate and alkali metal bisulfide.

Alkali metal N-methylaminobutyrates are useful as reactants in the preparation of poly(arylene sulfide). The most commonly used of the alkali metal N-methylaminobutyrates is sodium N-methylaminobutyrate (SMAB). Often, SMAB or other alkali metal N-methylaminobutyrates are prepared in situ in a reaction vessel to which a sulfur source and polyhalo substituted aromatic compounds are later added.

It has now been found that this valuable chemical intermediate can be produced continuously for use in a continuous process for making poly(arylene sulfide) or for storage or shipment for such a process. It has been further found that not only the alkali metal N-methylaminobutyrate can be made continuously, but also that complexes of this material with alkali metal bisulfide can be made continuously. The continuous preparation of this latter type of compound is particularly advantageous for use in the preparation of poly(arylene sulfide).

It is, therefore, an object of this invention to provide alkali metal N-methylaminobutyrate and alkali metal N-methylaminobutyrate-alkali metal bisulfide complex compositions which can be used as reactants in poly(arylene sulfide) production. It is also an object of this invention to provide a continuous process for the preparation of alkali metal N-methylaminobutyrate and complexes of this material and alkali metal bisulfide. It is still another object of this invention to provide a process for further treating alkali metal N-methylaminobutyrate and complexes of this material with alkali metal bisulfide to dehydrate the reaction mixture producing a product from which the water has been substantially removed. It is another object of this invention to provide a slurry of alkali metal N-methylaminobutyrate or a slurry of alkali metal N-methylaminobutyrate complexed with alkali metal bisulfide in N-methylpyrrolidone that is suitable for immediate use, shipping, or storage.

Other aspects, objects and the various advantages of this invention will become apparent upon reading this specification in conjunction with the drawing and the appended claims.

STATEMENT OF THE INVENTION

In accordance with this invention a method is provided for continuously producing alkali metal N-methylaminobutyrate in which an aqueous alkali metal hydroxide is contacted with N-methylpyrrolidone (NMP) in a stirred reactor at reaction conditions and for a time sufficient to produce a predominantly one-phase system and this predominantly one-phase reaction system is maintained at the same reaction conditions while it is passed through a disrupted flow-tube reactor for a time sufficient to complete the reaction producing alkali metal aminobutyrate and to attain an essentially one-phase system within the disrupted flow reactor.

In another embodiment of the invention alkali metal bisulfide, preferably having the same alkali metal as in the alkali metal hydroxide is present as the third component of the reaction mixture so that a reaction to produce a complex of alkali metal aminobutyrate and alkali metal bisulfide is substantially completed within the disrupted flow reactor.

In further embodiments of the invention the products, alkali metal aminobutyrate or a complex of alkali metal aminobutyrate and alkali metal bisulfide, is further treated to dehydrate the reaction mixture by retaining the reaction mixture in a first stage vessel at a temperature in the range of about 325° F. to about 375° F. and at a pressure in a range of about 10 psia to about 40 psia for a time sufficient partially to dehydrate the reaction mixture with subsequent treatment of the liquid effluent in a second stage dehydration process at a temperature in a range of about 350° F. to about 460° F. and a pressure in the range of about 10 psia to about 40 psia for a time sufficient substantially to remove water from the reaction mixture.

In a still further embodiment of the invention, the vapor overhead from the dehydration treatments is fractionated for separation of the water from NMP with the optional return of the NMP to the first stage dehydration.

In the process of this invention N-methylpyrrolidone is reacted with an alkali metal hydroxide in a reaction that proceeds according to the following reaction equation:

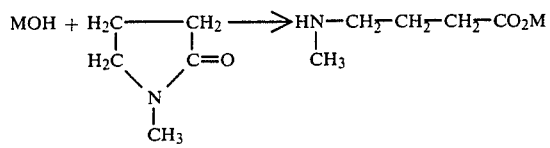

in which M is an alkali metal chosen from lithium, sodium, potassium, rubidium, and cesium, with a preferred alkali metal being sodium.

The reaction is preferably carried out in a dual reaction system in which the first zone is a stirred vessel and the second zone is a disrupted flow tube reactor. The dual system is used because the initial reactants form two separate phases which are most advantageously reacted in the presence of vigorous agitation, but which form a single phase reaction mixture before completion of the reaction. The single phase reaction mixture is well suited to passage through a disrupted flow tube reactor to provide the mixing at continuous reaction conditions to complete the reaction.

The reactions in both the stirred reactor and the pipe reactor are carried out at equal temperatures ranging from about 220° F. to about 310° F. and at a positive pressure of up to about 100 psig. The reaction time of the reactants in the stirred vessel and in the pipe reactor will depend upon the size of the reactors, but the reaction mixture is retained in the stirred reactor for a time sufficient to form a predominantly single phase reaction mixture, i.e., at least about 60 percent homogeneous single phase and then retained in the pipe reactor for a time sufficient substantially to complete the reaction.

When the alkali metal bisulfide is added to the reaction a 1:1 molar complex of alkali metal N-methylaminobutyrate and alkali metal bisulfide is formed. This complex has the formula

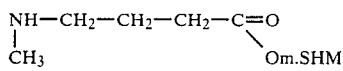

wherein M is chosen from the alkali metals named above, preferably sodium. The reaction is conducted at the same conditions to form the complex as were described above for forming the alkali metal N-methylaminobutyrate.

The alkali metal N-methylaminobutyrate complexed with alkali metal bisulfide formed by the process of this invention is principally useful in the preparation of poly(acrylene sulfide) such as that described in U.S. Pat. No. 4,060,520. With the addition of an alkali metal carboxylate as an optional ingredient, a poly(arylene sulfide) of low flow rate essentially as described in the procedure of U.S. Pat. No. 3,919,177 can be formed. The poly(arylene sulfide) most of interest that can be formed by using the reactants formed by the process of this invention is poly(phenylene sulfide) (PPS).

To provide the product of this invention in its most desirable form, further treatment by dehydration of the reaction mixture can be carried out. The dehydration is accomplished in a two-stage process in which the reaction mixture is subjected to a temperature in the range of about 260° F. to about 400° F. at a pressure of up to about 40 psia for a time sufficient to remove at least a portion of the water from the mixture with transfer of the liquid effluent from this first stage to a second stage vessel in which the temperature is maintained in a range of about 350° F. to about 460° F. using the same pressure as in the first stage to produce a kettle effluent comprising alkali metal N-methylaminobutyrate slurried in NMP substantially free of water.

BRIEF DESCRIPTION OF THE DRAWING

The invention can best be understood by discussion of the examples in conjunction with the drawing in which.

The following examples are meant to be illustrative and should not be taken as exclusive.

EXAMPLE I

Figure 1:
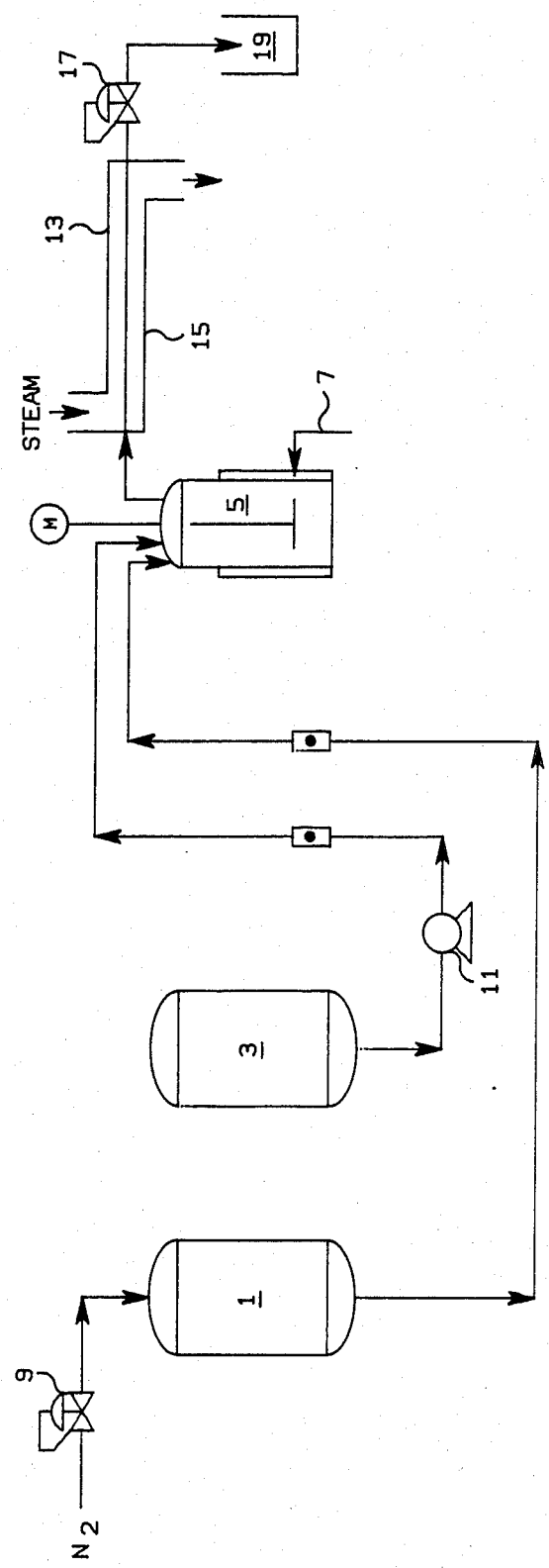
FIG. 1 is a line drawing of a pilot plant operation for the production of sodium N-methyl-aminobutyrate (SMAB) and FIG. 2 is a line drawing of a commercial-scale design for continuous process for producing SMAB.

Several pilot plant tests were run using a continuous reaction unit, as shown in FIG. 1, in which sodium hydroxide from a 5-gallon feed tank (1) and N-methyl-pyrrolidone (NMP) from a 55-gallon feed tank (3) are transferred to a stirred, one-liter steel autoclave (5) heated by means of an outside electric heater (7). Aqueous 50 weight percent sodium hydroxide was fed to the continuous reaction unit using a 60 psig differential pressure between the feed tank (1) and the unit (5). The sodium hydroxide feed tank was kept at a nitrogen pressure of about 150 psig and a temperature of 50° F. The nitrogen pressure was controlled by pressure control valve (9) admitting nitrogen to the sodium hydroxide feed tank (1). NMP was pumped from feed tank (3) by means of a Viking gear pump (11) with variable speed drive into the stirred autoclave (5). The reaction mixture exiting the stirred autoclave (5) was passed to a 15-foot long double-walled steel pipe reactor (13) filled with steel balls of ½" diameter and heated with steam supplied by steam jacket (15). Pressure was maintained on the entire system by control valve (17) on the outlet of the pipe reactor. Effluent from the pipe reactor passed from the system through valve (17) into a sample vessel (19).

The stirred autoclave (5) and the steel pipe reactor (13) were kept at equal temperatures ranging from 220° F. to 310° F. The residence time of NMP and aqueous sodium hydroxide in the stirred autoclave (5) and the pipe reactor (13) was about 8 to about 14 minutes.

Samples of the reaction mixture collected in the sample vessel 19 were taken every 15 minutes and analyzed by means of potentiometric titration using 1N hydrochloric acid and a Metrohm Herisau Potentiograph E 536. Sharp titration end points were obtained for the hydroxyl group of unreacted NaOH and for the amino group of SMAB.

EXAMPLE II

In this example the formation of SMAB in the continuous unit of Example I at various temperatures and feed rates is described. Average analysis results from 8 runs are summarized in Table I. The pressure was 85 psig for all runs.

TABLE I

| Run | NMP Feed Rate (cc/minute) | NaOH Feed Rate (cc/minute) | Reactor Temperature (°F.) | Residence Time Of Reactants (minutes) | Reactor Effluent Weight % of SMAB | Weight % of NaOh | SMAB/NaOH Weight Ratio |
| --- | --- | --- | --- | --- | --- | --- | --- |
| 1 | 90 | 18 | 310 | 14 | 36.8 | 0.28 | 131 |
| 2 | 90 | 32 | 310 | 12 | 50.5 | 0.71 | 71 |
| 3 | 125 | 60 | 300 | 8 | 64.2 | 1.27 | 51 |
| 4 | 125 | 60 | 290 | 8 | 59.5 | 1.16 | 51 |
| 5 | 125 | 60 | 280 | 8 | 57.2 | 1.60 | 36 |
| 6 | 125 | 60 | 270 | 8 | 51.0 | 1.53 | 33 |
| 7 | 125 | 60 | 250 | 8 | 45.6 | 2.55 | 18 |
| 8 | 125 | 60 | 220 | 8 | 0 | 18.8 | 0 |

Data in Table I show that, at reactor temperatures of 270°–310° F. and residence times of 8–14 minutes the reaction of NMP and NaOH produced SMAB at desirably high yields. At lower temperatures the reaction became slower and finally stopped completely at 220° F.

EXAMPLE III

Figure 2:
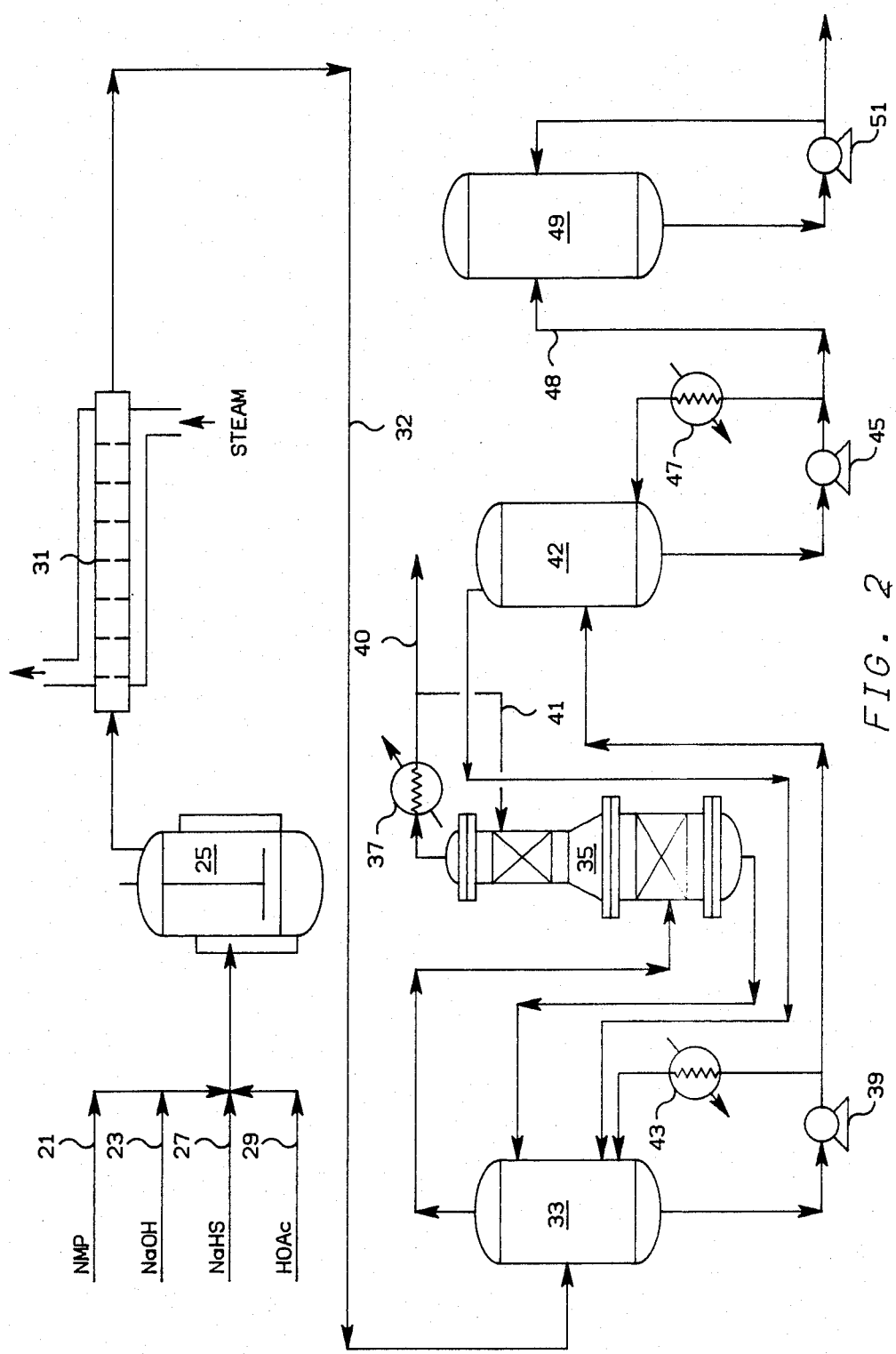

In this example is described the design of a commercial-scale continuous process for producing SMAB. The same process units can also be employed in producing a SMAB-NaHS complex, which can be utilized in synthesizing poly(phenylene sulfide) (PPS) by reaction with polyhalo aromatics. Referring now to FIG. 2 and detailing a process for producing SMAB-NaHS complex, NMP is charged through line (21) and aqueous NaOH is charged through line (23) to a stirred reactor (25) having an approximate diameter of 3.5 feet and an approximate height of 6.75 feet. The reactor is heated to about 300° F. NaHS is added to reactor (25) through line (27) for the formation of a 1:1 molar complex of SMAB and NaHS. Another optional ingredient added in this embodiment is acetic acid through line (29) which does not enter into the reaction to form a complex with the other materials but which is added to the reaction mixture to produce sodium acetate in-situ, used as an additive for the preparation of PPS of low flow rate.

The reaction mixture is then passed through a cylindrical, steam-heated static mixer (31) of about 8 inches diameter and about 20 feet of length having a plurality of baffle plates extending from the wall. The temperature of this second reactor is also about 300° F. and its function is to increase the residence time of the reactants so as to accomplish a more complete conversion to the SMAB-NaHS complex.

The completed reaction mixture is then passed through line (32) to the dehydration unit. The reaction mixture enters first stage dehydration vessel (33) which is maintained at a temperature of about 350° F. and a pressure about 25 psia. Vessel (33) has a diameter of about 4 feet and a height of about 6.75 feet. The overhead vapors from (33) pass to a fractionating column (35) having a column height of about 38 feet and a diameter ranging from about 24 inches (bottom part) to about 20 inches (top part). The overhead product from fractionating column (35) upon cooling in condensor (37) is essentially water, a portion of which is withdrawn through (40) as dehydration effluent and the remainder is returned through line (41) as reflux to the fractionator (35). The bottom product from fractionator (35) contains large amounts of NMP and is recycled to the first stage dehydration vessel (33).

The liquid bottom effluent from the first stage dehydration vessel (33) is pumped through pump (39) to a second stage dehydration vessel (42) of about the same size as the first stage dehydration vessel. A portion of said effluent from (33) is recycled through reboiler (43). The dehydration is essentially completed in second stage vessel (42) at about 436° F. and about 25 psia. The overhead product from second stage dehydration vessel (42) is recycled to first stage dehydration vessel (33). A portion of the bottom effluent from second stage dehydration vessel (42) is recycled through reboiler (47). The remainder of the effluent, is transferred through pump (45) and line (48) into the storage tank (49). The bottom effluent contains the desired reaction product—, in this example SMAB-NaHS— and is stored in tank (49) at about 400° F./25 psig until it is used for the production of PPS resin. Preferably a portion of said effluent is recirculated to (49) by means of pump (51) so as to avoid settling of solids in the tank.

Presented below in Table II are material balances for the production of SMAB, SMAB-NaSH, and SMAB-NaSH with sodium acetate according to the operation set out above. The material balances are referenced to flow rate in process lines identified in FIG. 2. For the purposes of Table II, the production of SMAB is case 1, the production of SMAB-NaSH in case 2, and the production of SMAB-NaSH with sodium acetate added is case 3.

TABLE II

| | | Line in | Flow Rate (lb/hr) | | |
| --- | --- | --- | --- | --- | --- |
| | Material | FIG. 2 | Case 1 | Case 2 | Case 3 |
| Feed | NMP | 21 | 7,500 | 7,500 | 7,500 |
| | NaOH | 23 | 2,000 | 1,000 | 1,200 |
| | H$_2$O | 23 | 2,000 | 1,000 | 1,200 |
| | NaSH | 27 | — | 1,410 | 1,410 |
| | H$_2$O | 27 | — | 940 | 940 |
| | HOAc | 29 | — | — | 300 |
| | H$_2$O | 29 | — | — | 90 |
| After Reaction | SMAB | 32 | 6,950 | — | — |
| | SMAB.NaHS | 32 | — | 4,880 | 4,930 |
| | NMP | 32 | 2,550 | 5,030 | 5,070 |
| | H$_2$O | 32 | 2,000 | 1,940 | 2,230 |
| | NaOAC | 32 | — | — | 410 |
| After Dehydration | SMAB | 48 | 6,950 | — | — |
| | SMAB.NaHS | 48 | — | 4,880 | 4,930 |
| | NMP | 48 | 2,550 | 5,030 | 5,070 |
| | NaOAC | 48 | — | — | 410 |
| | H$_2$O (with product) | 48 | 30 | 30 | 30 |
| | H$_2$O (drained) | 40 | 1,970 | 1,910 | 2,200 |

We claim:

1. A continuous process for producing alkali metal-aminobutyrate comprising:
   (a) contacting an aqueous alkali metal hydroxide with N-methylpyrrolidone in a stirred reactor at reaction conditions for a time sufficient to produce a predominantly one-phase system and
   (b) maintaining said reaction conditions while passing said predominantly one-phase system through a disrupted flow tube reactor at a rate substantially to complete the reaction within said disrupted flow reactor.

2. The process of claim 1 wherein the reaction temperature is in a range above about 240° F.

3. A process of claim 2 wherein the reaction temperature is in a range of about 240° to about 310° F.

4. A process of claim 1 wherein the alkali metal hydroxide is NaOH.

5. A process of claim 1 in which the effluent from said disrupted flow reactor is subjected to further treatment comprising:
   (c) dehydrating said effluent in a first stage reaction zone in a temperature range of about 260° F. to about 400° F., and
   (d) subjecting liquid effluent from said first stage dehydration zone to dehydration in a second stage dehydration zone at a temperature in a range of about 350° F. to about 460° F. to produce a kettle effluent comprising sodium N-methylaminobutyrate slurried in N-methylpyrrolidone substantially free of water.

6. A process of claim 5 wherein overhead effluents from both dehydration stages are fractionated to separate an overhead substantially of water and a kettle product substantially of N-methylpyrrolidone.

7. A process of claim 6 wherein said kettle product is recycled to said first stage dehydration.

8. A process of claim 6 wherein said kettle product is recycled to said first stage dehydration.

9. A continuous process for producing an alkali metal aminobutyrate-alkali metal bisulfide complex comprising:
   (a) contacting an aqueous alkali metal hydroxide and N-methylpyrrolidone with the bisulfide of the same alkali metal used in the metal hydroxide in a stirred reactor at reaction conditions for a time sufficient to produce a predominantly one-phase system and (b) maintaining said reaction conditions while passing said predominantly one-phase system through a disrupted flow tube reactor at a rate substantially to complete the reaction within said disrupted flow reactor.

10. A process of claim 9 wherein the reaction temperature is in a range of at least about 220° F.

11. A process of claim 10 wherein the reaction temperature is in a range of about 220° F. to about 310° F.

12. A process of claim 9 wherein the alkali metal hydroxide is NaOH and the alkali metal bisulfide is NaHS.

13. A process of claim 9 in which the effluent from said disrupted flow reactor is subjected to further treatment comprising:

(c) dehydrating said effluent in a first stage reaction zone in a temperature range of about 260° F. to about 400° F., and (d) subjecting liquid effluent from said first stage dehydration zone to dehydration in a second stage dehydration zone at a temperature in a range of about 350° F. to about 460° F. to produce a kettle effluent comprising sodium N-methylaminobutyrate slurried in N-methylpyrrolidone substantially free of water.

14. A process of claim 13 wherein overhead effluents from both dehydration stages are fractionated to separate an overhead substantially of water and a kettle product substantially of N-methylpyrrolidone.

* * * * *